United States Patent [19]

Bond et al.

[11] 4,047,928

[45] Sept. 13, 1977

[54] WILD OAT HERBICIDE MIXTURE

[75] Inventors: Richard P. M. Bond, Sittingbourne; Robert J. Pryce, Faversham; Clive A. Raven, Sittingbourne; Michael A. J. Venis, Faversham, all of England

[73] Assignee: Shell Oil Company, Houston, Tex.

[21] Appl. No.: 698,612

[22] Filed: June 21, 1976

[30] Foreign Application Priority Data

June 30, 1975 United Kingdom ............... 27483/75

[51] Int. Cl.$^2$ ............................................. A01N 9/02
[52] U.S. Cl. ........................................... 71/88; 71/92; 71/105; 71/107; 71/108; 71/110; 71/111; 71/115
[58] Field of Search ............................................. 71/88

[56] References Cited

U.S. PATENT DOCUMENTS

| | | | |
|---|---|---|---|
| 2,485,680 | 10/1949 | Wachs | 424/188 X |
| 2,485,681 | 10/1949 | Wachs | 424/188 X |
| 3,598,859 | 8/1971 | Yates et al. | 71/111 X |
| 3,761,508 | 9/1973 | Haddock | 71/111 X |
| 3,920,440 | 11/1975 | Takaoka et al. | 71/88 |

Primary Examiner—Joseph Paul Brust

[57] ABSTRACT

A selective wild oat herbicide composition comprising as active ingredient, a N,N-disubstituted alanine derivative and as a synergist, a methylenedioxyphenyl polyglycol ether.

12 Claims, No Drawings

WILD OAT HERBICIDE MIXTURE

BACKGROUND OF THE INVENTION

This invention relates to a wild oat herbicide composition and to a method of controlling wild oats in cereal crops.

Wild oats (Avena fatua) presents a major weed problem which plagues agricultural practice on a worldwide scale. Wild oat infestations are especially prevalent and difficult to control in cereal grain crops where competition from the wild oat is responsible for yield and economic losses amounting to many millions of dollars annually. In recognition of this problem, considerable agricultural research has been devoted, in the past, to the development of herbicidal compositions and methods to combat wild oat infestations in cereal crops.

An established family of compounds which has shown a very high level of activity towards wild oats and also a marked selectivity towards cereals is the N,N-disubstituted-alanine derivatives, for example, ethyl N-benzoyl-N-(3,4-dichloro-phenyl)-amino propionate (Suffix-herbicide) for use in wheat and isopropyl (+) -2-(N-benzoyl-3-chloro-4-fluoroanilino) propionate (Barnon-herbicide) for use in barley.

SUMMARY OF THE INVENTION

It has now been found that the activity of these N,N-disubstituted alanine derivatives may be greatly enhanced by means of a methylenedioxy-phenyl polyether which heretofore has been exclusively used as a synergist for insecticides especially pyrethrins. Surprisingly, it has been discovered that certain methylenedioxyphenyl polyethers which do not possess any herbicidal activity against wild oats, by themselves, can promote the herbicidal activity of the N,N-disubstituted alanine derivatives to a quite remarkable extent without affecting the selectivity thereof.

DESCRIPTION OF THE PREFERRED EMBODIMENTS

The present invention provides a selective wild oat herbicidal composition comprising as active ingredient, a N,N-disubstituted alanine derivative having the following general formula I:

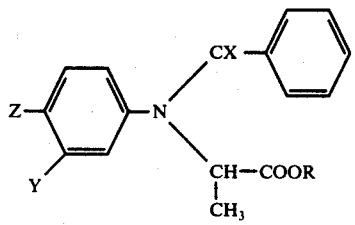

where Y and Z each represent chlorine or fluorine, R is a hydrogen atom or an alkyl group containing up to 6 carbon atoms, and X is oxygen or sulfur; and as a synergist therefor, a methylenedioxybenzene derivative having the following general formula:

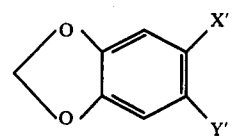

wherein Y' is hydrogen or an alkyl group containing up to 6 carbon atoms and X' is a polyglycol ether group containing up to 20 carbon atoms and 2 to 6 oxygen-ether linkages.

Especially preferred alanine derivatives are those having the following general formula II:

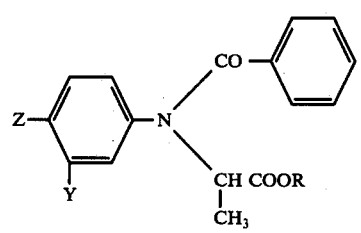

wherein Z represents chlorine or fluorine, Y is chlorine, and R is methyl, ethyl or isopropyl. Of these compounds the wild oat herbicide especially suited for use in barley crops is the compound of formula II above wherein:

Z = fluorine;
Y = chlorine; and
R = isopropyl.

The best compounds for use in wheat crops have the formula II above wherein:

Z = chlorine or fluorine;
Y = chlorine; and
R = methyl or ethyl.

The alanine derivatives can exist in optically-active forms and, generally the levo-rotatory isomer is the most active form; thus, where it is appropriate the alanine derivative may be employed in its most active optically-active form in the composition according to the invention.

The N,N-disubstituted alanine derivatives used in the present invention may be prepared by reacting the corresponding mono-N-substituted alanine derivative with a benzoyl halide. A more detailed description of the synthesis thereof can be found in U.S. Pat. Nos. 3,598,859 and 3,761,508.

Preferably, the methylenedioxyphenyl polyglycol polyether synergists of the present invention are the lower alkyl substituted methylenedioxybenzyl polyglycol ethers and the most preferred synergist is the compound having the formula:

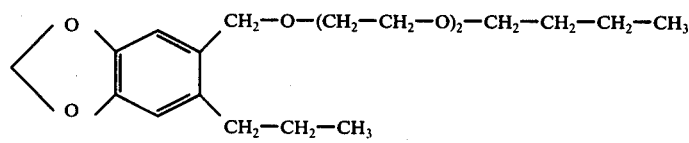

The methylenedioxybenzyl polyglycol ethers may be conveniently prepared by reacting a 3,4-methylenedioxybenzyl halide with the sodium salt of the corresponding polyglycol ether. Examples of these methylenedioxybenzyl polyglycol ethers and the methods of synthesis thereof can be found in U.S. Pat. Nos. 2,485,680 and 2,485,681.

As only the recorded synergistic activity of these methylenedioxybenzene derivatives concerns their use in relation to insecticides, it is quite remarkable that they should possess synergistic properties in the herbicidal field. It will be appreciated that, to be commercially useful wild oat herbicides must be selective in their action and must not produce any lasting harmful effects on the growing cereal crop to which they are applied; accordingly it is important that in any composition containing the herbicide, this balance of selectivity is not upset by the inter-action of other ingredients present in the composition. Suprisingly, the methylenedioxybenzyl polyglycol ether synergists of the present invention not only promote the herbicidal activity against wild oats but also do not have any deleterious effect on the cereal crop. Thus, the composition according to the invention can be used safely as a selective herbicide in wild oat infested cereal crops. The application of the herbicidal compositions of the present invention should be made in accordance with the established techniques for applying the alanine derivatives, that is to say at the time between the end of the cultivating stage and the appearance of the second node on the cereal crop.

With this invention it is possible to control wild oat over a wide range of its development by post-emergent foliar applications. Wild oat can be controlled in cereal crops by applicaton of from 0.05 to 2.0 lb/a active ingredient of the composition according to the invention wherein the weight ratio of the alanine derivative to the methylenedioxybenzene derivative is in the range 10:1 to 1:10, preferably in the range 5:1 to 1:1.

The herbicidal composition according to the invention may also employ a carrier, a surface active agent or both a carrier and a surface active agent to facilitate application of the composition to wild oat infested land at the desired dosage rates. The term "carrier" as used herein means a solid or fluid material, which may be inorganic or organic and of synthetic or natural origin.

Typical solid carriers include natural and synthetic clays and silicates for example, natural silicas such as diatomaceous earths and aluminium silicates, for example, kaolinites, montmorillonites, and micas. Typical fluid carriers are ketones, for example, methylcyclohexanone, aromatic hydrocarbons, for example, methylnapthalanes, petroleum fractions, such as, for example petroleum xylenes and light mineral oils, and chlorinated hydrocarbons, for example, carbon tetrachloride. Mixtures of liquids are often suitable.

One or more surface active agents and/or stickers can be included in the formulation. The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan sucrose or pentaerythritol, condensates of these with ethylene oxide and/or propylene oxide; condensation products of fatty alcohols or alkyl phenols for example p-octylphenol or p-octylcresol, with ethylene oxide and/or propylene oxide; sulphates or sulphonates of these condensation products, alkali or alkaline earth metal salts, preferably sodium salts, of sulphuric or sulphonic acid esters containing at least 10 carbon atoms in the molecule, for example, sodium lauryl sulphate, sodium secondary alkyl sulphates, sodium salts of suphonated castor oil, and sodium alkylaryl sulphonates such as sodium dodecylbenzene sulphonate; and polymers of ethylene oxide and copolymers of ethylene oxide and propylene oxide.

Aqueous dispersions and emulsions, for example, compositions obtained by diluting a wettable powder or a concentrate according to the invention with water, are also within the scope of the present invention. These emulsions may be of the water-in-oil or of the oil-in-water type, and may have a thick "mayonnaise"-like consistency.

The invention also includes a method of selectively controlling wild oat in cereal crops which comprises applying the composition according to the invention to a tract of land which is bearing cereal crops and infested with wild oat.

The compositions of this invention can be applied to the wild oat plants in a conventional manner. The dust and liquid compositions may be conveniently applied by the use of power-dusters, boom and hand sprayers, and sprayduster. The compositions can also be applied from airplanes as a dust or spray because of the effectiveness of the compositions at low dosages.

If desired the composition according to the invention may also be mixed with other wild oat herbicides, for example 4-chloro-2-butynyl-m-chlorocarbanilate (common name: barban; trade name: "Carbyne"), or methyl 2-chloro-3-(4-chloro-phenyl) propionate (common name: chlorphenprop methyl; trade name: "bidisin"), or 1,2-dimethyl-3,5-diphenylpyrazolium methyl sulphate (trade name: "Avenge").

Alternatively or additionally the composition according to the invention may include the so-called "hormone" weedkillers (the phyenoxyalkanoic acids, salts and esters) e.g. MCPA, CMPP and 2,4-DP and/or the broad-leafed herbicides e.g. Ioxynil, Bromoxynil and Bentazon.

The inventions are further illustrated in the following Examples:

EXAMPLE 1

The following compounds were tested for their activity as wild oat herbicides when mixed with 5-(2-(2-butoxyethyl)ethoxymethyl)-6-propyl-1,3-benzodioxole (common name: piperonyl butoxide) as synergist:

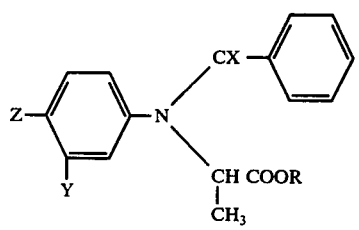

| Wild Oat Compound | X | Y | Z | R |
|---|---|---|---|---|
| A | O | Cl | F | isopropyl |
| B (levo-rotating isomer of A) | O | Cl | F | isopropyl |
| C | O | Cl | Cl | ethyl |
| D | O | Cl | F | methyl |

-continued

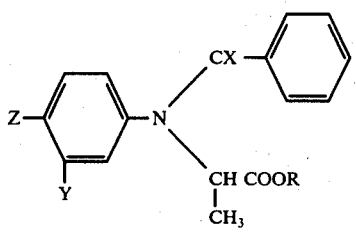

| Wild Oat Compound | X | Y | Z | R |
|---|---|---|---|---|
| E | O | Cl | Cl | isopropyl |
| F | O | Cl | F | ethyl |
| G | S | Cl | F | isopropyl |

The mixtures were made up into a sprayable solution by dissolving 1 g of the mixture in 4 ml of an emulsifiable concentrate formulation having the following composition:

Mineral oil — 100 g
Emulsifiers — 60 g
Cyclohexanone — 700 g
Orthoxylene — up to 1 liter The resulting formulations were then diluted with distilled water as required to obtain the required concentrations of active material.

A number of 2.7 in. pots of John Innes No. 1 compost were sown with 25-30 seeds of cultivated oat (*Avena*). When the plants had reached the 1½ leaf stage, a solution of the mixture under test was sprayed, using a logarithmic dilution sprayer, at five different doses for each species. Mixtures of different proportions of the compounds were also sprayed at five doses each.

Assessments were made 11 days after spraying. Phytotoxicity to the oat plants was assessed visually on a percentage scale (where 100 = no growth after spraying and 0 = growth of untreated control). These values were analysed by computor to calculate the growth inhibition dosages to give a 90% reduction for the oat plants, abbreviated to $GID_{90}$.

The results are given in the following table in which the last column gives the actual dosage in lb/a for the wild oat compound. It will be appreciated that the combined dosage rate of wild oat compound plus synergist can be calculated from these values by multiplying by a factor obtained from the compound:synergist weight ratio.

| Wild Oat Compound | Compound:Synergist Weight Ratio | $GID_{90}$ (lb/a) for wild Oat Compound in the mixture |
|---|---|---|
| A | 1:0 | 0.312 |
|   | 2:1 | 0.232 |
|   | 4:1 | 0.241 |
| B | 1:0 | 0.152 |
|   | 2:1 | 0.107 |
|   | 4:1 | 0.116 |
| C | 1:0 | 0.312 |
|   | 2:1 | 0.152 |
|   | 4:1 | 0.170 |
| D | 1:0 | 0.143 |
|   | 2:1 | 0.098 |
|   | 4:1 | 0.098 |
| E | 1:0 | 1.151 |
|   | 2:1 | 0.758 |
|   | 4:1 | 0.99 |
| F | 1:0 | 0.086 |
|   | 2:1 | 0.073 |
|   | 4:1 | 0.064 |
| G | 1:0 | 1.204 |
|   | 2:1 | 0.250 |

-continued

| Wild Oat Compound | Compound:Synergist Weight Ratio | $GID_{90}$ (lb/a) for wild Oat Compound in the mixture |
|---|---|---|
|   | 4:1 | 0.241 |

From the results shown above it can be seen that the presence of the synergist gives rise to a significant increase in the activity of the wild oat compound in that the dosage required to give a 90% reduction in plant growth is always less than when the synergist is absent.

Tests have established that the synergist by itself at the dosage rates employed in this example has no phytotoxic action and moreover the selective properties of the wild oat compounds are in no way impaired by the presence of the synergist in the mixture.

What is claimed is:

1. A herbicidal composition comprising as active ingredient an N,N-disubstituted alanine derivative having the following general formula:

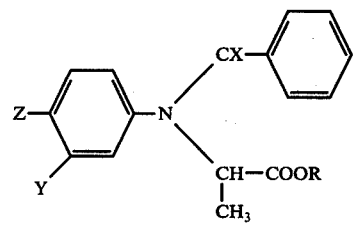

wherein Y and Z each represent, fluorine or chlorine, X is oxygen or sulfur; and R is hydrogen or an alkyl group containing up to 6 carbon atoms; and as a synergist therefor, a methylenedioxybenzene derivative having the following general formula:

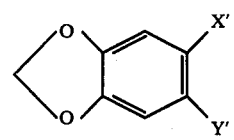

wherein X' is a polyglycol ether group containing up to 20 carbon atoms and 2 to 6 oxygen-ether linkages and Y' is hydrogen or an alkyl group containing up to 6 carbon atoms, said alanine derivative and methylenedioxybenzene derivative being present at a weight ratio of the alanine derivative to the methylenedioxybenzene derivative of from 10:1 to 1:10.

2. The herbicidal composition of claim 1 wherein the substituent Z of the N,N-disubstituted alanine derivative is chlorine or fluorine; Y is chlorine; R is methyl, ethyl or isopropyl and X is oxygen.

3. The herbicidal composition of claim 2 wherein Z is fluorine; Y is chlorine; and R is isopropyl.

4. The herbicidal composition of claim 2 wherein Z is chlorine or fluorine; Y is chlorine; and R is methyl or ethyl.

5. The herbicidal composition of claim 1 wherein the methylenedioxybenzene derivative is 3,4-methylenedioxy-6-propylbenzyl n-butyl diethyleneglycol ether.

6. The herbicidal composition of claim 2 wherein the methylenedioxybenzene derivative is 3,4-methylenedioxy-6-propylbenzyl n-butyl diethylene glycol ether.

7. The method of selectively controlling wild oats comprises applying to the wild oat infested soil an effective amount of the herbicidal composition of claim 1.

8. The method of selectively controlling wild oats comprises applying to the wild oat infested soil an effective amount of the herbicidal composition of claim 2.

9. The method of selectively controlling wild oat comprises applying to the wild oat infested soil an effective amount of the herbicidal composition of claim 3.

10. The method of selectively controlling wild oat comprises applying to the wild oat infested soil an effective amount of the herbicidal composition of claim 4.

11. The method of selectively controlling wild oat comprises applying to the wild oat infested soil an effective amount of the herbicidal composition of claim 5.

12. The method of selectively controlling wild oat comprises applying to the wild oat infested soil an effective amount of the herbicidal composition of claim 6.

* * * * *